United States Patent [19]
McKeon

[11] Patent Number: 6,133,734
[45] Date of Patent: Oct. 17, 2000

[54] METHOD AND APPARATUS FOR EVALUATING AN EARTH FORMATION USING NUCLEAR MAGNETIC RESONANCE TECHIQUES

[75] Inventor: Donald C. McKeon, Katy, Tex.

[73] Assignee: Schlumberger Technology Corporation, Houston, Tex.

[21] Appl. No.: 09/000,745

[22] Filed: Dec. 30, 1997

[51] Int. Cl.$^7$ .................................................. G01V 3/00
[52] U.S. Cl. .......................................... 324/303; 324/309
[58] Field of Search .................................. 324/303, 300, 324/307, 309

[56] References Cited

U.S. PATENT DOCUMENTS

| | | | |
|---|---|---|---|
| 4,528,508 | 7/1985 | Vail, III | 324/303 |
| 4,656,422 | 4/1987 | Vail, III et al. | 324/303 |
| 4,710,713 | 12/1987 | Strikman | 324/303 |
| 4,724,385 | 2/1988 | Vail, III | 324/303 |
| 4,804,918 | 2/1989 | Vail, III | 324/303 |
| 5,363,041 | 11/1994 | Sezginer | 324/303 |
| 5,428,291 | 6/1995 | Thomann et al. | 324/303 |
| 5,596,274 | 1/1997 | Sezginer | 324/303 |

FOREIGN PATENT DOCUMENTS

| | | |
|---|---|---|
| WO 97/01110 | 1/1997 | WIPO . |
| WO 97/14063 | 4/1997 | WIPO . |

OTHER PUBLICATIONS

DV Trushkin, OA.Shushakov & AV Legchenko, "Surface NMR Applied to an Electroconductive Medium," *Geophysical Prospecting 43*, pp. 623–633 (1995).

OA Shushakov, "Surface NMR Measurement of Proton Relaxation Times in Medium to Coarse–Grained Sand Aquifer," *Magnetic Resonance Imaging*, v. 14, Nos. 7/8, pp. 959–960 (1996).

SC Bushong, "Gradient Echo Imaging," *Magnetic Resonance Imaging, Physical and Biological Principles*, 2$^{nd}$ Ed., Mosby Press, NY, pp. 279–297 (1995).

BF Melton & VL Pollack, "Optimizing Sudden Passage in the Earth's–Field NMR Technique," *J. Magnetic Resonance*, Series A 122, pp. 42–49 (1996).

I Solomon, "Rotary Spin Echoes," *Physical Rev. Letters*, v. 2, No. 7, pp. 301–302 (Apr. 1, 1959).

EJ Wells & KH Abramson, "High Resolution NMR Rotary Echoes," *J. Magnetic Resonance 1*, pp. 378–392 (1969).

T Hwang, PCM van Zijl & M Garwood, "Fast Broadband Inversion by Adiabatic Pulses," *J. Magnetic Resonance 133*, pp. 200–203 (1998).

M Garwood & K Ugurbil, "B$_1$ Insensitive Adiabatic RF Pulses," *NMR Basic Principles and Progess*, v. 26, Springer–Verlag, NY NY, pp. 109–147 (1992).

A Tannus & M Garwood, "Improved Performance of Frequency–swept Pulses using Offset–Independent Adiabaticity," *J. Magnetic Resonance*, Series A 120, pp. 133–137 (1996).

(List continued on next page.)

*Primary Examiner*—Christine K. Oda
*Assistant Examiner*—Brij B. Shrivastav
*Attorney, Agent, or Firm*—John J. Ryberg; Brigitte L. Jeffery

[57] ABSTRACT

This invention makes an NMR measurement at extended depths into the formation using the earth's magnet field to generate an NMR measurement and using a magnet field from a permanent magnetic to suppress the NMR signal in the borehole and shallow formation. The magnetic field from a permanent magnet increases the Larmor frequency in the borehole and the shallow earth formation. An oscillator applies an RF magnetic field to the formation for a period of time in order to align nuclei spins approximately perpendicular to the earth's magnetic field. At the end of this period, the field is turned off rapidly. Since the spins are unable to follow this sudden change, they are left aligned perpendicular to the earth's field. These nuclei precess about the earth's field at the approximate Larmor frequency of the earth's field. The RF receiver detects the RF signals in the approximate frequency range of the Larmor frequency. Borehole and shallow formation protons precessing at the high frequencies resulting from the permanent magnet are not detected by the receiver. Therefore, the receiver only detects signals from greater depths in the earth's formation.

16 Claims, 3 Drawing Sheets

OTHER PUBLICATIONS

E Kupce & R Freeman, "Optimized Adiabatic Pulses for Wideband Spin Inversion," *J. Magnetic Resonance*, Series A 118, pp. 299–303 (1996).

T Hwang & AJ Shaka, "Water Suppression that Works, Excitation Sculpting using Arbitrary Waveforms and Pulsed Field Gradients," *J. Magnetic Resonance*, Series A 112, pp. 275–279 (1995).

MH Levitt & R Freeman, "Compensation for Pulse Imperfections in NMR Spin–Echo Experiments," *J. Magnetic Resonance 43*, pp. 65–80 (1981).

VL Ermakov, J–M Bohlen & G Bodenhausen, "Improved Schemes for Refocusing with Frequency–Modulated Chirp Pulses," *J. Magnetic Resonance*, Series A 103, pp. 226–229 (1993).

S Conolly, D Nishimura & A Macovski, "A Selective Adiabatic Spin–Echo Pulse," *J. Magnetic Resonance 83*, pp. 324–334 (1989).

M Garwood & Y ke, "Symmetric Pulses to Induce Arbitrary Flip Angles with Compensation for RF Inhomogeneity and Resonance Offsets," *J. Magnetic Resonance 94*, pp. 511–525 (1991).

T–L Hwang, PCM van Zul & M Garwood, "Broadband Adiabatic Refocusing without Phase Distortion," *J. Magnetic Resonance 124*, pp. 250–254 (1997).

RA de Graaf, K Nicolay & M Garwood, "Single–Shot $B_1$–Insensitive Slice Selection with a Gradient–Modulated Adiabatic Pulse, BISS–8," Center for Magnetic Resonance Research and Dep't of Radiology, Univ. of Minn. Medical School, Minneapolis, Minnesota, pp. 652–654 (1996).

A Abragam, "Macroscopic Aspects of Nuclear Magnetism," *The Principles of Nuclear Magnetism*, Ch. III, pp. 65–68; 86; Fig's III5 and III6, Clarendon Press, Oxford (1961).

DMS Bagguley, ed., "Imaging by Nuclear Magnetic Resonance," *Pulsed Magnetic Resonance*: NMR, ESR, and Optics, Ch. 14, pp. 317–345, Clarendon Press, Oxford (1992). (Based on a review by P. Mansfield in J. Phys. E., 21, 18 (1988)).

S Conolly, G Glover, D Nishimura & A Macovski, "A Reduced Power Selective Adiabatic Spin–Echo Pulse Sequence," *Magnetic Resonance in Medicine 18*, pp. 28–38 (1991).

RA Webb, "New Technique for Improved Low–Temperature Squid NMR Measurements," *Rev. Sci. Instrum.*, v. 48, No. 12, pp. 1585–1594 (Dec. 1977).

RR Ernst, G Bodenhausen & A Wokaun, "One–Dimensional Fourier Spectroscopy," *Principles of Nuclear Magnetic Resonance in One and Two Dimensions*, Chapter 4, pp. 90–239, Clarendon Press, Oxford (1987).

R.C. Herrick, S.H. Couturie & D.L. Best, "An Improved Nuclear Magnetism Logging System and Its Application to Formation Evaluation", Sep. 23–26, 1979, Las Vegas, Nevada, SPE8361.

METHOD AND APPARATUS FOR EVALUATING AN EARTH FORMATION USING NUCLEAR MAGNETIC RESONANCE TECHIQUES

FIELD OF THE INVENTION

This invention relates to the evaluation of an earth formation using nuclear magnetic resonance techniques, an more particularly to a method and apparatus for determining nuclear magnetic resonance characteristics of an earth formation at extended depths in a formation.

BACKGROUND OF THE INVENTION

Nuclear Magnetic Resonance (NMR) refers to a physical response of nuclei to a magnetic field. NMR is one of the most common techniques used today to examine the content of a material. One application of NMR techniques is in the evaluation of an earth formation during formation drilling and logging operations. In operation, today's standard logging NMR tool produces a static magnetic field and directs this field into an earth formation of interest. Researchers have recognized that some particles of an earth formation such as atomic nuclei and protons have magnetic spins that tend to align with a static magnetic field $B_0$ imposed on a formation. The tool produces this magnetic field with one or more magnets. By configuring the combined magnetic fields of a set of magnets in the NMR tool and then directing the magnetic field into the formation, hydrogen nuclei in the formation align with the magnetic field generated by the magnets. When the magnetic field is removed, the nuclei return to their original orientation giving off a radio-frequency signal. Tool equipment records the amplitude of the radio-frequency signal as the free-fluid index, which is an indication of the amount of water or hydrocarbons that are not bound to any surface in the formation Basic Principles of Nuclear Magnetic Resonance The hydrogen atom is of primary importance in NMR techniques because of its high natural occurrence in hydrocarbons. The hydrogen atom consists of a single proton (the nucleus) and an electron orbiting around the proton. In the classical picture, the proton rotates (spins) around its axis; this rotation results in angular momentum $Ih'$, where I is called the spin and $h'$ is Planck's constant h divided by $2\pi$. The angular momentum is a measure of angular motion expressed by the product of the momentum of inertia of the nucleus and the angular velocity $\omega_{rot}$. The rotation (spinning) generates a magnetic moment $\mu$. In the absence of an external magnetic field, the individual magnetic moment in an ensemble of hydrogen nuclei (protons) are randomly oriented. However, in an externally applied magnetic field $B_0$, the magnetic moments of the protons are forced to be aligned so that the net magnetization (total magnetic moment/volume) is either parallel or anti-parallel with the direction of the field. The magnetic moments of the individual protons precess around the axis $B_0$ at a specific angular frequency $\omega_0$ (Larmor frequency). The Larmor frequency is determined by the magnitude of $B_0$ according to the equation $\omega_0 = \gamma B_0$, where $\gamma$ is the gyromagnetic ratio which is related to $\mu$ by $\gamma = \mu/h'I = 42.58$ MHz/T for protons. (The Larmor frequency is the frequency at which gyromagnetic moments precess in a magnetic field. Atoms and nuclei posses magnetic moments because of their spin and precess like small gyroscopes about the direction of an externally applied steady magnetic field (such as the earth's field). Radio-frequency energy at right angles to the steady field will be absorbed because of resonance when the RF-frequency equals the precession frequency.) At thermal equilibrium, the number $N_p$ of protons whose z component of magnetic moment is oriented parallel to the direction of the magnetic field is slightly greater than the number $N_a$ of antiparallel protons, depending on $B_0$ and the sample temperature T. The slight preponderance of parallel protons results in a net nuclear macroscopic magnetization $M_0$ which is the resultant of the individual magnetic moments in the sample, along the direction of $B_0$.

In order to detect $M_0$ it is necessary to irradiate the formation with an RF magnetic field $B_1$ at approximately the same frequency as the Larmor precession frequency $\omega_0$, but applied perpendicular to $B_0$ by an angle $\theta$. If the applied ratio frequency (RF) magnetic field $B_1$ is turned off (thereby forming a pulse), the magnetization $M_0$ precesses around the direction of $B_0$. According to Faraday's induction law, the precessing magnetization $M_0$ induces a voltage in a coil wound with its axis in the process plane and tuned to the Larmor frequency $\omega_0$. The voltage induced in the coil is detected as the NMR signal. The hydrogen nuclei (protons) of water and hydrocarbons occurring in rock pores produce NMR signals that are distinct from any signals induced in other rock constituents. A population of such nuclei having a net magnetization, tends to align with any imposed field such as $B_E$.

Earlier NMR tool's, such as Schlumberger's NML™ nuclear magnetic logging tool (See U.S. Pat. No. 4,035,718 issued to Richard N. Chandler) uses the earth's magnetic field and at least one multi-turn coil wound on a core of a non-magnetic material. The coil is coupled to the electronic circuitry of the tool and is designed to periodically apply a strong DC polarizing magnetic field, $B_P$, to the formation in order to align spins approximately perpendicular to the earth's field, $B_E$. The characteristic time constant for the exponential buildup of this spin polarization is called the spin-lattice relaxation time, $T_1$. At the end of polarization, the field is rapidly terminated. Since the spins are unable to follow this sudden change, they are left aligned perpendicular to $B_E$ and therefore precess about the earth's field at the Larmor frequency $f_L = \gamma B_E$, where $\gamma$ is the gyromagnetic ratio of the proton. The Larmor frequency in the earth's magnetic field varies from approximately 1300 to 2600 Hz, depending on location. The spin precession induces in the coil a sinusoidal signal of frequency $f_L$ whose amplitude is proportional to the number of protons present in the formation.

The NMR tool is usually deployed in a borehole and is surrounded by borehole fluid. This fluid material also generates a signal that can affect the tool's measurements. Because the resonance region of an electromagnetic signal extends into the borehole, the signal and more specifically a magnetic resonance signal is produced in the borehole fluid. Such a magnetic resonance signal from the borehole fluid is detected along with the desired NMR signal. This borehole signal must be eliminated or reduced because the NMR device functions by detecting protons in fluids. Typically, the rock formation is 0–30% fluid by volume, but the borehole fluid contains more than 50% fluid which has a high density of hydrogen nuclei. For this reason, the magnetic resonance signal of the borehole fluid would dominate any formation signal detected by the pulsed NMR device. One solution to borehole interference is to add fluid additives, such as magnetite, to the borehole fluid to suppress the borehole fluid signal, thereby preventing the fluid signal from obscuring the formation signal. However, the logistic difficulty of doping the mud contributed to the infrequent use of the earlier NMR logging tool.

Another obstacle in NMR logging is the shape of the borehole wall. As shown in FIG. 1, in an ideal logging situation, the borehole wall 1 would have a uniform and straight shape. This uniform borehole wall would enable a nuclear magnetic resonance tool 2 to be positioned in close proximity with the formation 3 surrounding the borehole and there would be minimal tool standoff 4. A uniform borehole 5 also reduces the effect that the borehole signal has on the actual measurement. However, in an actual logging situation, the borehole wall 1 can have the shape shown in FIG. 2. In this type of borehole, tool standoff 4 and borehole effects are greatly increased by the borehole wall shape.

While the early generation of NMR tools have the capability to extract information about the earth formation and fluid properties, these tools and techniques have some disadvantages which limit their utility in practical applications. With the newer NMR tools, because of the requirement of the application of the RF field, the precession frequency is fixed, and the depth of investigation from the borehole into the formation of the nuclear magnetic properties is restricted to a shallow region of the formation around the borehole wall, approximately 1 to 3 inches. Therefore, there is a need for a nuclear magnetic resonance system and method that will extend the depth of investigation into the formation of the NMR measurement.

SUMMARY OF THE INVENTION

It is an object of this invention to increase the depth of investigation into an earth formation of an NMR measurement.

It is another object of this invention to decrease the NMR measurement signal from the borehole and the NMR signal from shallow formation depths.

The present invention uses the earth's magnetic field and a powerful permanent magnet to measure the NMR signal of a formation. However, instead of using the magnet to make the NMR measurement, as is the common NMR technique, the function of the permanent magnet is to suppress or "spoil" the NMR signal from the borehole and from shallow formation depths. The permanent magnet increases the Larmor frequency of the nuclei in the borehole and shallow formation such that the NMR signals in these regions are not detected by the NMR tool receiver. This suppressed area is called a "blind zone".

NMR signals at depths in a narrow region beyond the suppressed blind zone of the formation are detected by the receiver. The optimal NMR signal is obtained when the transmitter and receiver operate at the Larmor frequency for hydrogen nuclei. The Larmor frequency for hydrogen nuclei depends on the magnetic field strength, $B_0$ and is expressed as:

$$f_L[\text{Hz}] = 4258\, B_0[\text{Gauss}]$$

The magnitude of the signal depends on the transmitter power, $B_0$ field strength, region of investigation, temperature and hydrogen density. The new NMR measurement has a small $B_0$-field strength, but has a larger region of investigation.

The actual depth of the blind zone into the formation will depend on the actual tool design, magnet design and the temperature of the logging environment during the logging operation. The blind zone is the result of a large B-field applied close to the tool. In the blind zone, the Larmor frequency greatly exceeds the tool operating signal so no NMR signal is detected in the region of this large B-field. In the transition zone of the formation, which is at an extended depth in the formation, the applied B-field is within a few percent of the Larmor frequency of the hydrogen nuclei, therefore this region of the formation begins to contribute to the measured NMR signal. In the response signal, there would be a large blind zone, followed by a transition region with a peak in the response, followed by a region where the signal drops off rapidly until it is negligible. The tool measurement response reaches a peak and then begins to drop due to the attenuation of the $B_1$ RF field (the $B_1$ field tips the hydrogen nuclei and starts the precession process). Far from the borehole, the tool response drops to a negligible value. The ability of this tool to measure at extended depths into the formation will make this tool less sensitive to tool standoff in the borehole, borehole rugosity, and mud particle invasion.

DETAILED DESCRIPTION OF THE INVENTION

The present invention takes an NMR measurement of an earth formation using a concept similar to tuned a radio receiver. A radio receiver detects signals of a specific frequency or frequency range. The detected frequency depends on the tuning of the radio receiver. The receiver does not detect signals outside the tuned frequency range. In the present invention, the receiver in an NMR tool detects signal from nuclei in an earth formation that precess at frequencies in the approximate range of the Larmor frequency of hydrogen nuclei. This frequency will typically be in the range of 1300 Hz to 2600 Hz. This frequency range is a result of the fact that the earth's magnetic field strength varies in different geographic locations. Frequencies above and below the Larmor frequency range for hydrogen remain undetected and therefore do not affect the NMR measurement.

In the present invention, permanent magnets cause nuclei in the borehole and shallow formation materials to precess at frequencies that are substantially above the Larmor frequency of hydrogen nuclei. Therefore, the borehole and shallow formation nuclei precess at frequencies outside the range detected by the receiver, thereby suppressing and excluding the borehole and shallow formation NMR signals from the NMR measurement. The distant formations generate signals at the Larmor frequencies, however due to attenuation in the signals resulting from the distance the signals travels to the receiver, the signals from the distant formations also remain undetected at the receiver. However, there is a region of the formation that has frequencies in the range of the Larmor frequency for hydrogen nuclei. The receiver detects signals at these frequencies. Therefore, the NMR measurements come from this region of the formation and results in a measurement at a deeper formation depth than previous NMR tools.

Figure 1:
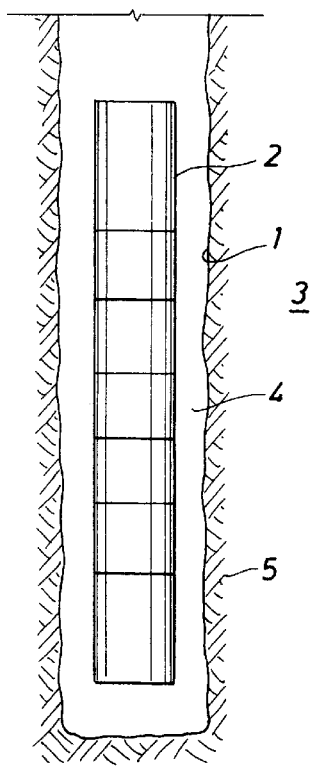
FIG. 1 shows a logging tool suspended in a uniform borehole.
Figure 2:
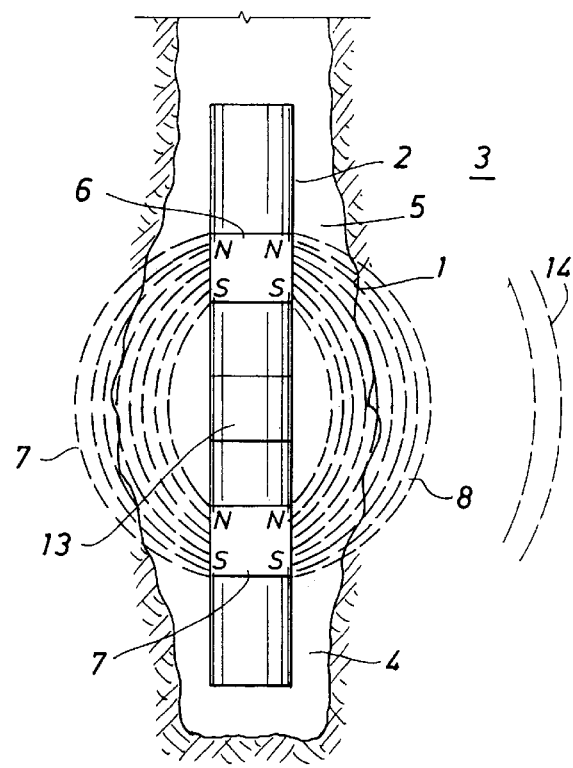
FIG. 2 shows a logging tool suspended in an non-uniform borehole with magnetic field lines.
Figure 3:
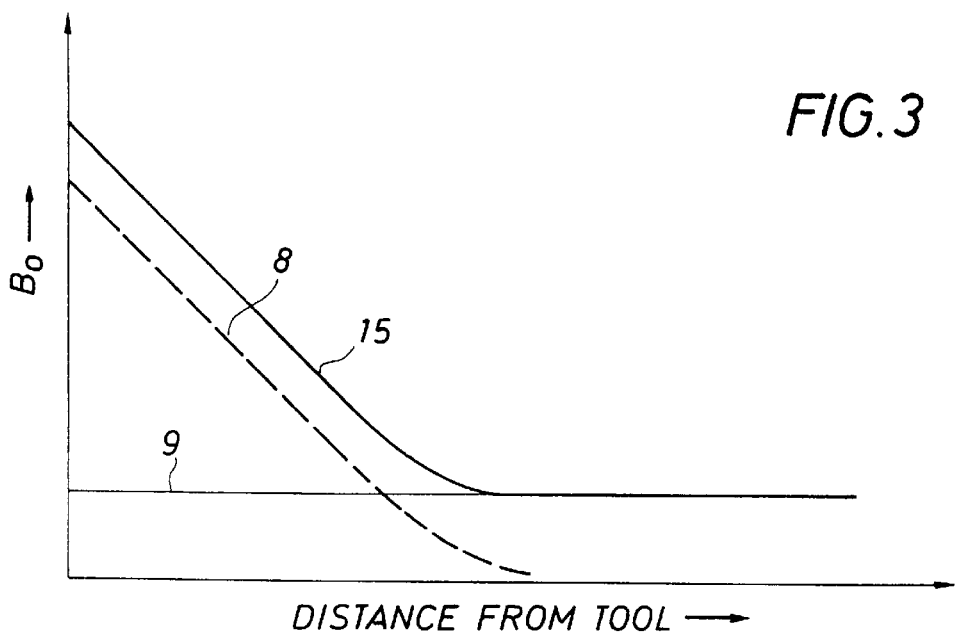
FIG. 3 shows a plot of the magnetic fields during the operation of the present invention.

As illustrated in FIG. 2, to perform this measurement, permanent magnets 6 and 7 create a magnetic field 8 in the borehole 5 and formation 3. The magnetic field is strongest at the borehole and decreases in strength as the depth into the formation increases. The earth formation also has a magnetic field that is uniform and remains constant regardless of the distance from the tool. FIG. 3 shows the progression of the two magnetic fields with distance from the borehole. As shown, the formation magnetic field 9 remains constant. However, the magnetic field 8 generated by the permanent magnet decreases with an increase in distance from the borehole.

In operation, the magnetic field 8 from the permanent magnet configuration 6 and 7 is applied to the formation 3. This field causes the nuclei in the earth formation and borehole to precess. The frequency of the precession of the nuclei will vary depending on the strength of the magnetic field applied to the nuclei. As the distance from the magnet increases, the effect of the magnetic field from the permanent magnet on the precession of the nuclei begins to decrease. The nuclei in the borehole material and formation closest to the permanent magnet will precess at a higher frequency than the nuclei farther in the formation. The magnetic field generated by the magnets 8 combines with the earth's magnetic field 9 to produce a resultant magnetic field curve 15.

Figure 4:
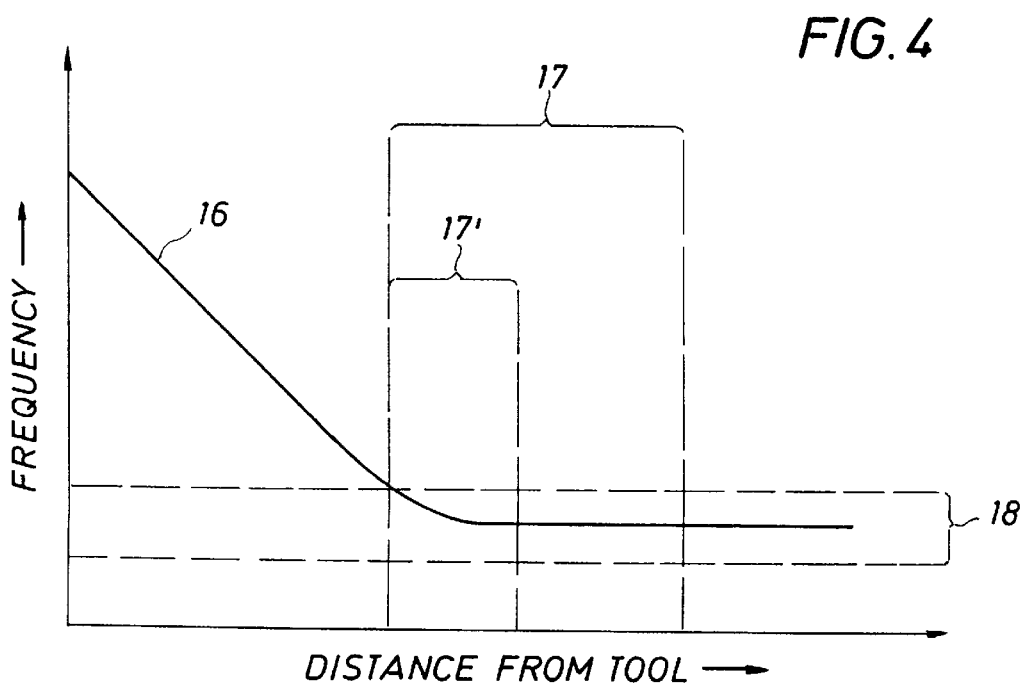
FIG. 4 shows a plot of the Larmor frequency range versus distance in the formation.

An antenna (transmitter/receiver) 13, in the tool, applies a strong RF magnetic field, $B_1$, to the formation in order to align nuclei spins approximately perpendicular to the earth's magnetic field. The characteristic time constant for the exponential buildup of this spin polarization is called $T_1$ (spin-lattice relaxation time). The polarizing field must be applied long enough for full polarization to occur. This time period is roughly five times the $T_1$ time constant. At the end of polarization, the RF magnetic field is turned off rapidly. Since the spins are unable to follow this sudden change, they are left aligned perpendicular to the earth's magnetic field (HE) and therefore process about the earth's field at the Larmor frequency, $$f_L = \gamma H_E, \qquad [1]$$

where γ is the gyromagnetic ratio of the nuclei (γ=4.2576× $10^3$ HzG). FIG. 4 shows a plot of the Larmor frequency 16 extending from the borehole into the formation. The Larmor frequency begins higher closer to the borehole and decreases in value as it extends further into the formation. At a certain distance in the formation, the Larmor frequency becomes constant, similar to the earth's magnetic field. As previously stated, the Larmor frequency in the earth's magnetic field varies roughly from 1300 to 2600 Hz, depending on the location of the formation and the depth in the formation.

Referring to FIG. 4, in a region 17 of the formation referred to as the "detection region", the Larmor frequency of the spin of the nuclei in the formation resulting from the application of the B-field will begin to approach the detection frequency range 18. Part of the detection region is a transition region 17' which can be viewed as the region where the Larmor frequency is above the Larmor frequency due to earth's magnetic field but still within the detectable limits of the tool.

The spin precession induces in a receiver a sinusoidal signal of frequency $f_L$, whose amplitude is proportional to the number of protons in the formation at this frequency. Inhomogeneities in the magnetic field cause the spins to dephase as they precess, resulting in an exponentially decaying sine wave with time constant $T_2$ and frequency $f_L$. The induced sinusoidal signal is representative of nuclei precessing at a frequency range close to the Larmor frequency. These nuclei are located in the detection region 17 of the formation. As mentioned, the permanent magnet causes the nuclei in the borehole fluid and shallow formation to precess at frequencies much greater than the Larmor frequency. As a result, the nuclei in these areas do not contribute to the induced sinusoidal signal and ultimately the NMR measurement. The detection region 17, from which the NMR signal is measured, is at a depth farther into the formation than distances at which conventional NMR tools can detect NMR signals.

Figure 5:
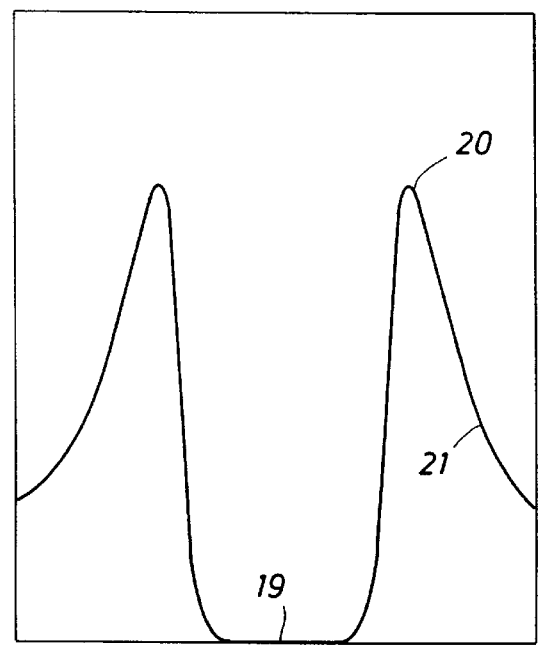
FIG. 5 shows the response of the NMR signal in the present invention.

FIG. 5 shows the detected signal in the present invention. In this signal, there is a large blind zone 19 where there is no signal. This blind zone is followed by a detection region with a peak 20 in the response. This detection region is followed by a region 21 where the signal drops off rapidly until it is negligible. The tool measurement response reaches a peak 20 and then begins to drop due to the attenuation of the RF field. Far from the borehole, the tool response drops to a negligible value. The ability of this tool to make measurements at extended depths into the formation will make this tool less sensitive to tool standoff in the borehole, borehole rugosity, and mud particle invasion.

The permanent magnets in the present invention can be configured in various arrangements. The objective of the magnet configuration is to have the magnetic field lines be as perpendicular as possible to the earth's magnetic field. FIG. 2 shows an example of a magnet configuration and the ideal shape of the lines 14. In this configuration, the tool has two permanent magnets 6 and 7 respectively on both ends of an antenna 13. In FIG. 2, the earth's magnetic field is aligned vertically with the borehole.

Although an embodiment of the present invention has similarities to the NML tool, the NML tool measurement derived its unique quality from the dependence of the nuclei relaxation time $T_1$ on the environment, as described in SPE Paper 8361, 1979. Hydrogen protons in solids or bound to surfaces have very short characteristic relaxation times, generally a few hundred microseconds at most. Bulk fluids in the pore space, however, have much longer relaxation times, usually hundreds of milliseconds. Since the observed free induction decay $T_2$ must be less than or equal to $T_1$, one effectively discriminates against matrix and bound nuclei by delaying observation of the signal until 25–30 ms after the beginning of free precession. Hence, only bulk or "movable" fluid in the pore is measured by the NML tool. The measurement presented by the log is thus called the fluid free index (FFI) or free fluid porosity ($\phi_f$). This quantity is derived from the extrapolated signal amplitude at the beginning of free precession. In order to reduce the relaxation time of the borehole fluids, the drilling mud is treated with a magnetite slurry before logging. Because of the very small signals involved in nuclear magnetism logging, sophisticated processing is necessary to extract the desired information.

A second embodiment of the present invention incorporates features of the Combinable Magnetic Resonance (CMR) tool. This method applies an oscillating magnetic field $B_1$ to the formation in order to align nuclei spins approximately perpendicular to the earth's field. However, this method has a different scheme for applying the oscillating magnetic field. A pulse sequence controls the oscillating magnetic field. U.S. Pat. No. 5,023,551 which is incorporated by reference, describes a typical pulse sequence for use in this method. This pulse sequence permits simultaneous measurement of T1 and T2. The preferred pulse sequence is:

$$[W_i-180\ \tau_i-90-(t_{cp}-180-t_{cp}-\text{echo})_j]_i \quad [2]$$

where j=1,2, . . . J, where J is the number of echoes collected in the CPMG (Carr-Purcell-Meiboom-Gill) sequence and is typically on the order of one or two hundred (typically CMR tools run at 600 to 1200), but always greater than ten; i=1,2, . . . I, where I is the number of recovery times; $W_i$ are waiting times; $\tau_I$ are recovery times, and $t_{cp}$ is the Carr-Purcell spacing. Measurements of the signals induced are made of each of a predetermined number of echoes. In a preferred embodiment, each echo measurement of the CPMG sequence is a measurement of the integrated amplitude of the echo, rather than a measurement of the greatest amplitude of the received echo. Determinations of T1, T2 and amplitude ($M_0$) are then made from the measurements. From one or more of the T1, T2 and amplitude determinations, formation parameters such as porosity and permeability may be derived according to equations known in the art.

As with the other embodiment, in operation, the permanent magnets 11 and 12 cause the nuclei in the borehole and shallow formation to spin at a frequency higher than the receiver frequency. The RF oscillating magnetic field is focused on the portion of the formation of interest in a direction that is perpendicular to the earth's magnetic field. The oscillating magnetic field tips the protons in the hydrogen nuclei of fluids within the formation. The angle through which spins are tipped is controlled by the strength of the $B_1$ field and the length of time $B_1$ is on. When the protons are tipped 90° from the direction of the earth's magnetic field, they precess in the plane perpendicular to the earth's magnetic field. In this method, initially all the protons precess in unison. While doing so they generate a small magnetic field at the Larmor frequency which is detected by the antenna and forms the basis for the NMR measurements. However, the earth's magnetic field is not perfectly homogeneous, therefore the protons to precess at slightly different frequencies. Gradually, they the protons lose synchronization and dephase causing the antenna signal to dephase. This decaying signal is called the free induction decay (FID) and the decay time is called T2 which is related to petrophysical properties such as movable fluid porosity, pore size distribution and permeability.

The procedure in the present invention is to apply 180° pulses in an evenly spaced train, as close together as possible. The entire pulse sequence, a 90° pulse followed by a long series of 180° pulses is called the CPMG sequence (see U.S. Pat. No. 5,023,551.) The antenna detects the T2 time for the region of the formation having a Larmor frequency of the antenna receiver.

Figure 6:
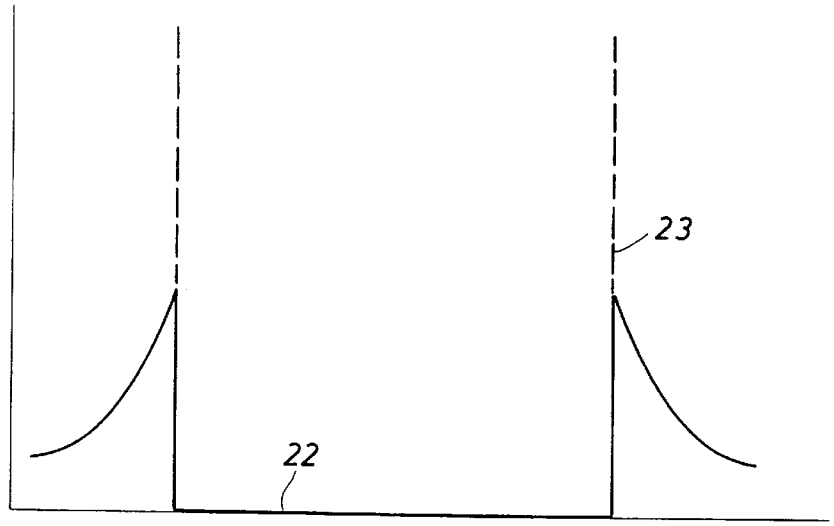
FIG. 6 shows a signal affected by borehole suppression techniques.
Figure 7:
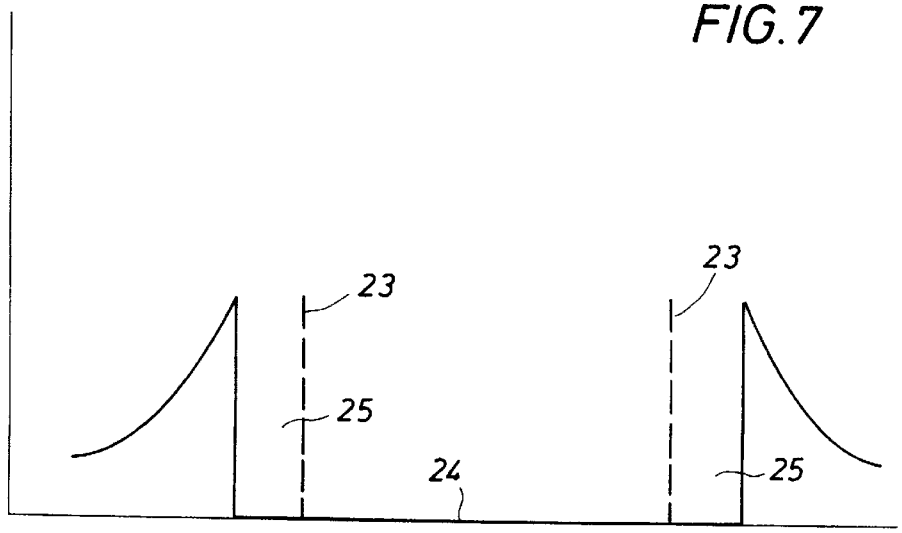
FIG. 7 shows a signal affected by suppression techniques of the present invention.

The present invention provides an advantage over prior tools that attempted to suppress borehole signals during NMR measurements in that this invention can extend the suppressed area from the borehole into the formation. As shown in FIG. 6, 22 is an ideal suppressed borehole signal. The suppression of this signal stops at the borehole wall 23. The signal 24 from the present invention, shown in FIG. 7, is extended passed the borehole wall 23 and into the earth's formation 25. Prior methods of borehole suppression would involve doping the borehole fluid with chemicals. However, these chemicals had no effect on the formation.

The present invention can also be used either as a focused or unfocused Logging While Drilling (LWD) operations.

The main objective of the invention in this application will be the same as previously described herein, which is to take a formation NMR measurement at extended depth of investigation into the formation. Again, this process would be through the use of "suppression" magnets.

It now will be recognized that new and improved methods and apparatus have been disclosed which meet all the objectives and have all the features and advantages of the present invention. Since certain changes or modifications may be made in the disclosed embodiments without departing from the inventive concepts involved, it is the aim of the appended claims to cover all such changes and modifications falling within the true scope of the present invention.

What is claimed is:

1. A method for making nuclear magnetic resonance (NMR) measurements in an earth formation from a tool located in a borehole traversing said formation comprising the steps of:
    (a) generating a static magnetic field in the formation to induce precession of nuclei in the borehole and shallow and deep volumes of said formation at a frequency higher than the frequency of a receiver in said borehole;
    (b) producing oscillating magnetic fields in said formation in order to induce signals in said formation which are measurable by said tool in said borehole; and
    (c) detecting induced signals from nuclei in the formation that rotate at frequencies approximately equal to the frequency of the receiver and thereby excluding signals from said borehole and shallow volume of said formation.

2. The method of claim 1 further comprising the step (d) of determining from said detected signals an indication of characteristics of said formation.

3. The method of claim 1 wherein said nuclei rotation in the borehole and shallow earth formation is increased by applying a permanent magnetic field to said borehole and shallow formation.

4. The method of claim 3 wherein said magnetic field decreases in intensity as the depth into the formation increases.

5. The method of claim 1 wherein said rotation frequencies approximately equal to the receiver frequency are in a detection region of the formation.

6. The method of claim 5 wherein said detection region is in a range of approximately 5 to 7 inches into the formation.

7. The method of claim 1 wherein said frequency of said receiver is the Larmor frequency of hydrogen.

8. The method of claim 1 wherein said step of radiating said volume includes using an RF antenna to radiate focused oscillating fields in the direction of said volume.

9. The method of claim 1 wherein an oscillation period of said oscillating magnetic field is sufficient to enable full polarization to occur.

10. The method of claim 9 wherein said full polarization period is approximately five times the $T_1$ time constant.

11. The method of claim 1 wherein said oscillating magnetic field has a pulse sequence of $$[W_i-180\ \tau_i-90-(t_{cp}-180-t_{cp}-\text{echo})_j]_i$$

where j=1,2, . . . J, where J is the number of echoes collected in the CPMG (Carr-Purcell-Meiboom-Gill) sequence and is typically on the order of one to several hundred, but always greater than ten; i=1,2, . . . I, where I is the number of recovery times; $W_i$ are waiting times; $\tau_I$ are recovery times, and $t_{cp}$ is the Carr-Purcell spacing.

12. The method of claim 1 wherein said nuclear magnetic resonance (NMR) measurements are made in an earth formation during logging while drilling operations.

13. An apparatus for investigating a characteristic of an earth formation traversed by a borehole, comprising a body adapted for movement in the borehole comprising:
   (a) magnet means for producing a static magnetic field in the borehole and shallow and deep volumes of said formation, said magnetic field decreasing in strength as the depth of the formation increases;
   (b) antenna means for radiating said formation with oscillating magnetic fields; and
   (c) a receiver for detecting signals from nuclei in the formation that rotate at frequencies approximately equal to the frequency of the receiver and thereby excluding signals from the borehole and shallow volume of said formation.

14. The apparatus of claim 13 wherein said antenna means comprises an antenna mounted on one side of said magnet means.

15. The apparatus of claim 14 wherein said antenna is operable both to produce oscillating magnetic fields and to detect signal in a region of the formation where precession is at the approximate Larmor frequency of hydrogen, said detected signals being representative of nuclear magnetic precession in said formation.

16. The apparatus of claim 13 wherein said magnet means comprises a plurality of permanent magnets affixed to said body in a predetermined configuration.

* * * * *